US006799573B1

(12) United States Patent
Bonner

(10) Patent No.: US 6,799,573 B1
(45) Date of Patent: Oct. 5, 2004

(54) AIR FILTRATION SYSTEM

(76) Inventor: James D. Bonner, 2605 Wright Rd., Akron, OH (US) 44320

(*) Notice: Subject to any disclaimer, the term of this patent is extended or adjusted under 35 U.S.C. 154(b) by 0 days.

(21) Appl. No.: 10/325,071

(22) Filed: Dec. 20, 2002

(51) Int. Cl.[7] .......................... A62B 23/02; A61M 16/00

(52) U.S. Cl. ............................ 128/205.27; 128/205.29; 128/206.12; 128/200.11; 128/200.13; 55/355; 96/234; 96/243

(58) Field of Search ....................... 128/200.11, 200.12, 128/200.13, 204.14, 205.27, 204.16, 205.12, 206.12, 205.29, 200.14; 55/355, DIG. 35, DIG. 33; 96/155, 234, 243, 205.12; 285/316, 308

(56) References Cited

U.S. PATENT DOCUMENTS 1,170,526 A * 2/1916 Gaither ......................... 96/118
1,196,539 A * 8/1916 Goldberg ............... 128/200.11
2,088,720 A * 8/1937 Poliniak ................ 128/200.13
3,980,080 A * 9/1976 Muto .................... 128/200.13
4,146,026 A * 3/1979 Montalvo .............. 128/200.13
4,213,769 A * 7/1980 Nagelmeyer .................. 96/247
5,724,964 A 3/1998 Brunson et al. ....... 128/206.19
5,836,303 A 11/1998 Hurst et al. ............ 128/206.24
5,848,592 A 12/1998 Sibley .................... 128/205.27
5,941,244 A 8/1999 Yamazaki et al. ..... 128/206.19
6,055,983 A 5/2000 Metzger ................ 128/206.17
6,338,340 B1 1/2002 Finch et al. ........... 128/205.27

* cited by examiner

*Primary Examiner*—Henry Bennett
*Assistant Examiner*—Mital Patel
(74) *Attorney, Agent, or Firm*—John D. Gugliotta; Olen L. York, III

(57) ABSTRACT

An air filtration system includes a light weight container which stores a quantity of water for filtering contaminants from inhaled air. A coupling assembly is used to connect the container to a flexible hose for delivery of the filtered air to the dust mask worn by the user. The coupling assembly allows a user to interchange one light weight container with another in a quick and convenient manner if one container becomes saturated with contaminants. A user simply pulls downward on the slidable jacket to release the industrial plug and allowing the attachment of another container to the hose via the coupling assembly.

14 Claims, 4 Drawing Sheets

AIR FILTRATION SYSTEM

RELATED APPLICATIONS

The present invention was first described in Disclosure Document Registration 509,922 filed on Apr. 15, 2002 under 35 U.S.C. §122, 37 C.F.R. §1.14 and MPEP § 1706. There are no previously filed, nor currently any co-pending applications, anywhere in the world.

BACKGROUND OF THE INVENTION

1. Field of the Invention

The present invention relates generally to an air filter for consumer or commercial use and, more particularly, to such an air filter utilizing an easily cleanable and replaceable fluid filtration medium.

2. Description of the Related Art

Various types of dust masks and air filtration systems have been placed on the market in an attempt to better protect the nasal lining and the lungs of people that work in contaminated environments. Such devices include paper filter dust masks, passive respirators, positive pressure respirators, and self-contained breathing apparatuses.

Paper filter dust masks are inexpensive products, since the dust masks are essentially a cupped paper filter with a rubber band-type fastener. However, the paper filter is generally effective for use only in low to moderately contaminated environments. Use of paper filter dust masks in an environment moderately or heavily contaminated yields poor results and includes plugging of the paper filter, facial skin irritation, or nasal and lung irritation. This low yield result of paper filter dust masks requires that individual paper filter dust masks are replaced frequently, which results in added cost to consumers to replace the product. In addition, the collective quantity of paper filter dust masks disposed of are environmentally unfriendly.

Passive respirators are generally manufactured from silicon rubber and contain several filtering elements, including paper or cloth filtering elements for trapping air particulates and absorbent filtering elements for trapping harmful or irritating gases. Like the paper filter dust masks, passive respirators are easily plugged in moderately or heavily contaminated environments, requiring frequent replacement of the filtering elements and adding additional costs to consumers. Plugging of the filtering elements restricts air flow and may cause the user to become uncomfortably hot result in facial skin irritation.

Positive pressure respirators are expensive, and under most circumstances, unnecessary. Although a positive pressure respirator yields much better results than either a paper filter dust mask or a passive respirator, a positive pressure respirator is generally required only in extreme circumstances, such as in the presence of harmful gases or the lack of oxygen. The positive pressure respirators are a poor alternative because of the expense, and maintenance, while the extreme circumstances required for use are infrequent.

A self-contained breathing apparatus yields optimal results in heavily contaminated environments. However, the self-contained breathing apparatus is very heavy for the average person to use effectively, weighing in at around fifty pounds. A self-contained breathing apparatus is generally constructed of very sturdy and expensive material, making the initial cost of the system very expensive in comparison to the other air filtration devices described above. In addition, the self-contained breathing apparatus is not easily serviceable by the user, resulting in added cost to the user.

The present invention is aimed at improving air filtration in contaminated environments, and offer an air filtration system that is simultaneously cost effective, light weight, portable, easily replaceable and easily disassembled.

A search of the prior art did not disclose any patents that read directly on the claims of the instant invention; however, the following references were considered related.

U.S. Pat. No. 6,338,340, issued in the name of Finch et al., describes a filter mask that includes a three-part solid paper filter mechanism;

U.S. Pat. No. 6,055,983, issued in the name of Metzger, describes a respirator filtration device incorporating a pocketed filter insert;

U.S. Pat. No. 5,941,244, issued in the name of Yamazaki et al., describes a mask filter designed to seal against the user's nose and chin to prevent dust intrusion;

U.S. Pat. No. 5,848,592, issued in the name of Sibley, describes the use of a water chamber through which air is passed in order to trap particulates;

U.S. Pat. No. 5,836,303, issued in the name of Hurst et al, describes a respirator apparatus incorporated within a whole-head garment; and U.S. Pat. No. 5,724,964, issued in the name of Brunson et al., describes a disposable face mask that has a filter body that seals around a user's nose and face.

Consequently, there exists a continuous need for new product ideas and enhancements for existing products in the air filtration industry.

SUMMARY OF THE INVENTION

It is therefore an object of the present invention to provide an improved air filtration system.

It is a feature of the present invention to provide an improved air filtration system that combines inexpensive and long-lasting components completely integrated to provide a convenient and safe means for filtering contaminants from contaminated air.

Briefly described according to one embodiment of the present invention, an air filtration system is provided that allows for easy assembly and use. The air filtration system includes a light weight container which stores a quantity of water for filtering contaminants from inhaled air. A coupling assembly is used to connect the filtered air to a flexible hose for delivery of the filtered air to the dust mask worn by the user. The coupling assembly allows a user to interchange one light weight container with another in a quick and convenient manner if one container becomes saturated with contaminants. A user simply pulls downward on the slidable jacket to release the Industrial plug and allowing the attachment of another container to the hose via the coupling assembly.

The use of the present invention provides users with all of the materials and tools necessary to ensure that when working in a contaminated environment, the user will feel safe and may inhale outside air because the water will work as the filter.

An advantage of the present invention is that it is specifically adapted for personal use because of the light weight components and the use of inexpensive materials.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the FIGS. 1–5.

1. Detailed Description of the Figures

Figure 1:
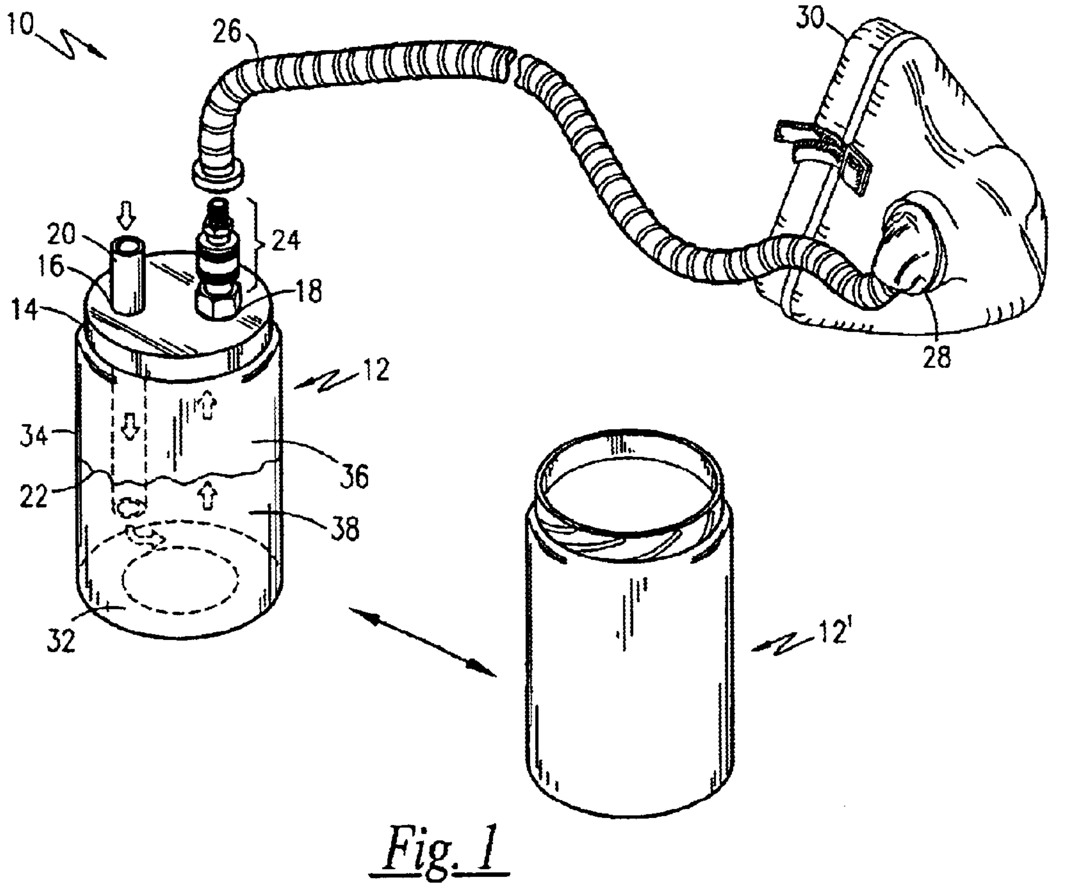
FIG. 1 is an exploded perspective view of an air filtration system.

Referring now to FIG. 1, an air filtration system 10 is shown, according to the present invention, an includes a water chamber 12, preferably constructed from plastic or another similar material, threadably coupled with a cap 14, with the cap 14 forming an air inlet aperture 16 and an air outlet aperture 18. A linearly elongated air outlet tube 20 extends from outside the water chamber 12, into and through the cap 14 and into the water chamber 12 at a position below the water level 22. An air outlet assembly 24 is coupled to and depending from the air outlet opening 18 and the cap 14. The air outlet assembly 24 is further coupled to a flexible hose 26. The hose 26 is further coupled to a mask coupling assembly 28. The mask coupling assembly 28 is further coupled to an air mask 30.

Figure 2:
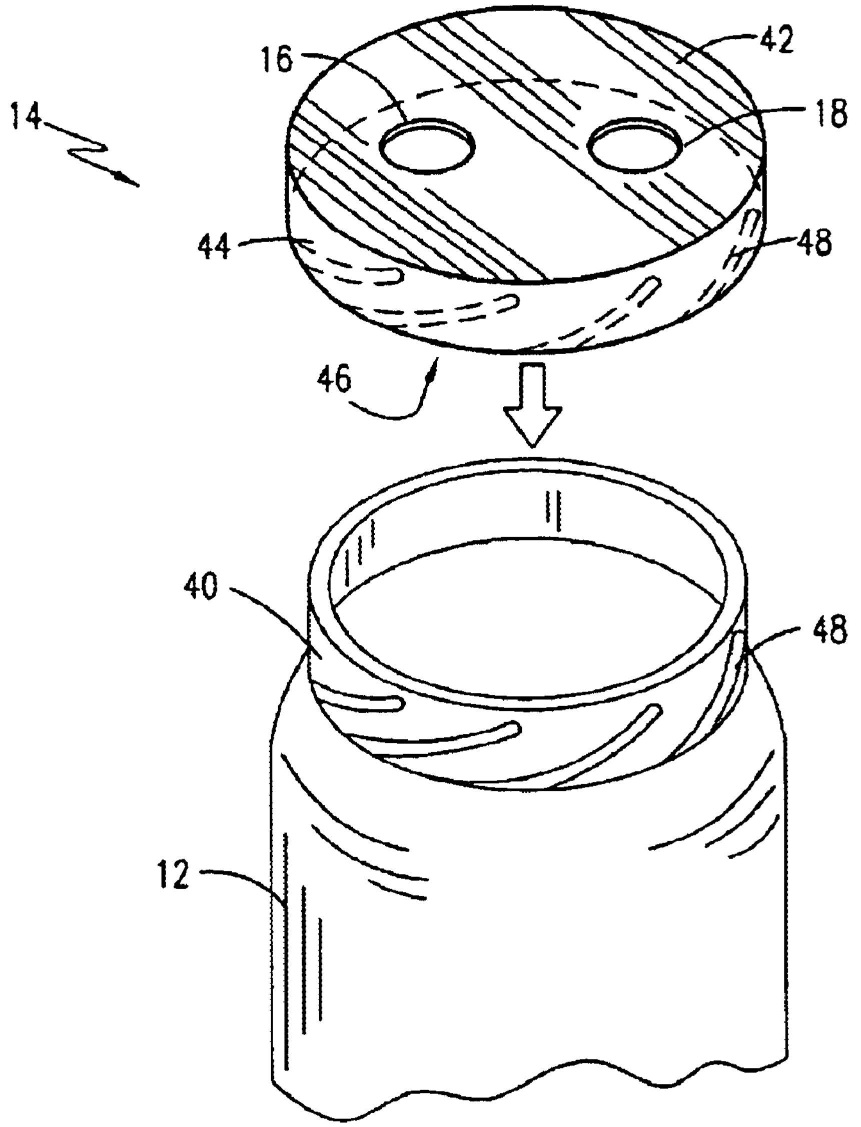
FIG. 2 is an exploded perspective view of the water chamber and the corresponding cap.

The water chamber 12 includes a planar base 32 perpendicularly engaged with a curvilinear chamber wall 34, with the planar base 32 and chamber wall 34 forming an internal chamber cavity 36 capable of receiving a quantity of water 38 and the linearly elongated air outlet tube 20. Referring specifically to FIG. 2, the top portion of the chamber wall 34 Includes an arcuate wall lip 40, which has threads 48 along the external circumference of the wall lip 40 for threadably coupling with a cap 14.

Referring now to FIG. 1 and FIG. 2, the cap 14 includes a planar cap top 42 perpendicularly engaged with a curvilinear cap wall 44, with the planar cap top 42 and the cap wall 44 forming a cap space 46. The cap 14 has threads 48 along the internal circumference of the cap wall 44, which threadably couple with the threaded wall lip 40 to provide a closed arrangement of the cap 14 and water chamber 12. The cap 14 also forms an air inlet aperture 16, lying along the same linear plane as the cap top 42, and capable of receiving and housing an linearly elongated tube 20. The cap 14 also forms an air outlet aperture 18, lying along the same linear plane as the cap top 42 and the air inlet aperture 16, and capable of receiving and housing an air outlet assembly 24. In the one embodiment, shown here, the cap top 42 is of a sufficient thickness so as to provide a suitable number of threads within the air outlet aperture 18 to allow the air outlet assembly 24 to be threadably coupled to the cap top 42 and the air outlet aperture 18.

Figure 3:
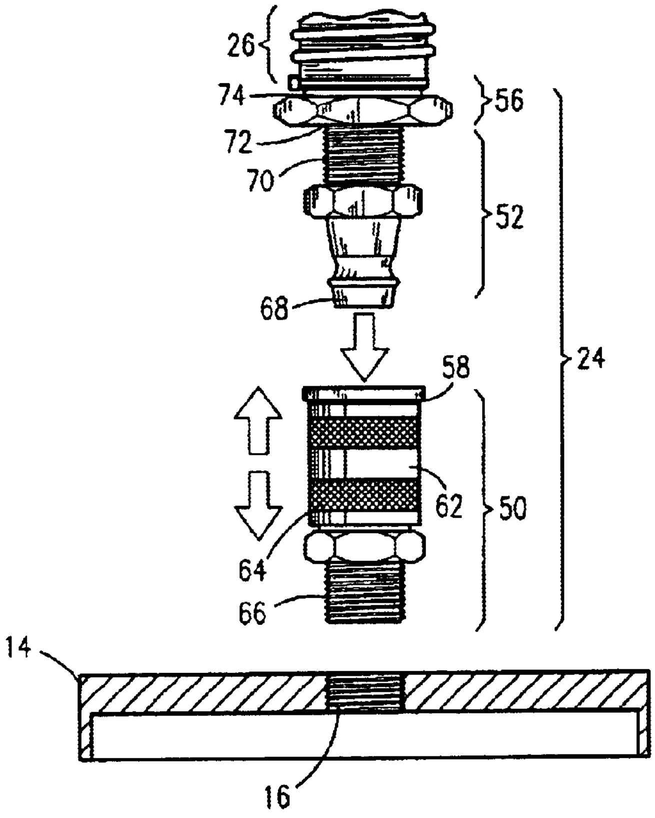
FIG. 3 is a side view of the air outlet assembly.
Figure 4:
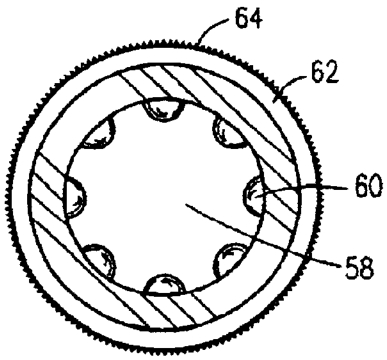
FIG. 4 is a top view of the industrial coupler illustrating the ball-bearing system used to securely hold the industrial plug when inserted.

In one embodiment of the present invention, shown in FIG. 3 and FIG. 4, the air outlet assembly 24 includes an industrial coupler 50 receiving an industrial plug 52, and the industrial plug 52 is threadably attached to a female coupler 56. The industrial coupler 50, the industrial plug 52 and the female coupler 56 are common to the art of coupling, and may be found in any hardware or home improvement store. The industrial coupler 50 includes a cavity 58 at the upper end, capable of receiving the plug nipple 68, and housing a plurality of ball-bearings 60 (see FIG. 4) for securely retaining the plug nipple 68. The industrial coupler 50 also includes a slidable jacket 62, with gripping tines 64, which release or close the internal ball-bearings 60 and allow the plug nipple 68 to be moved or securely held. The industrial coupler 50 also includes a threaded male portion 66 for threading the industrial coupler 50 into the air inlet aperture 16 of the cap 14. The industrial plug 52 includes a plug nipple 68 and an opposable threaded top portion 70. The female coupler 56 includes a female opening 72, for receiving the threaded top portion 70, and a tongue 74 for insertion into a hose 26.

Figure 5:
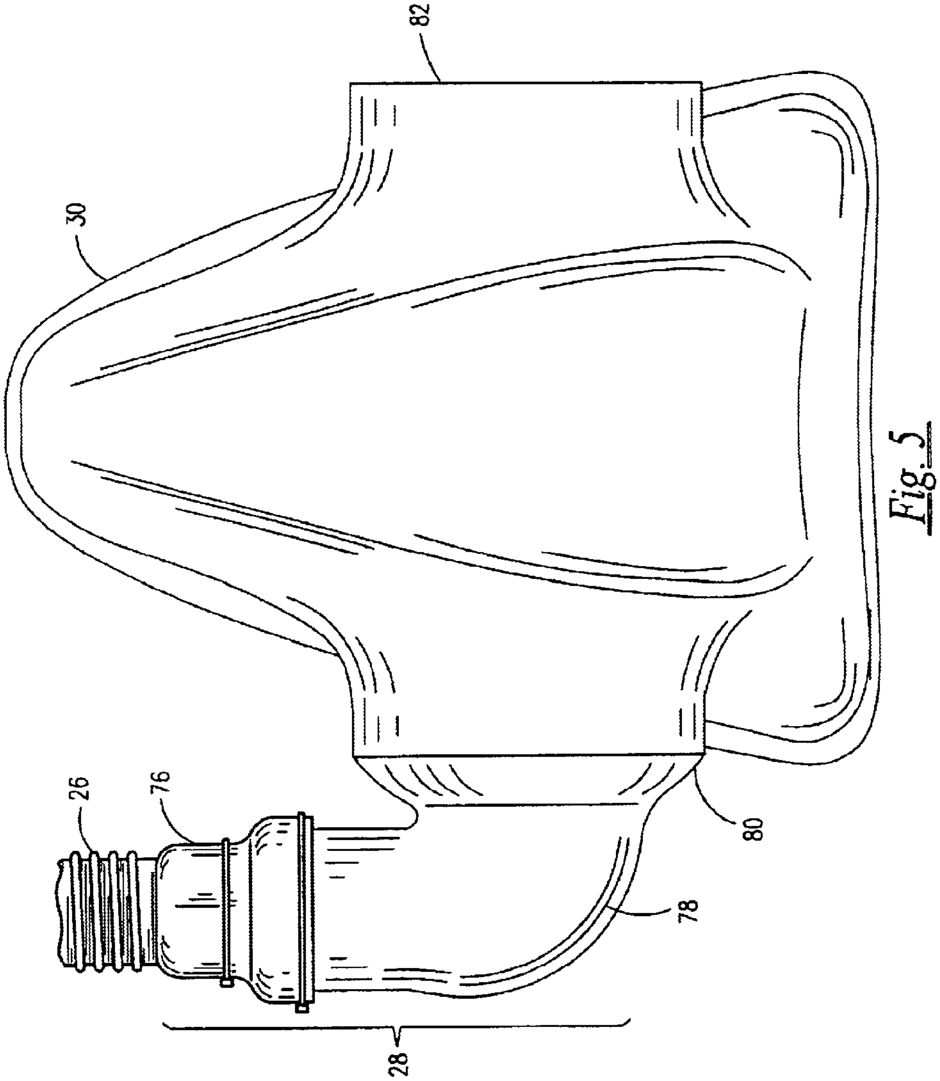
FIG. 5 is a side view of the mask coupling assembly illustrating the connectivity of the hose to the water dust mask and the mask cylinder.

Referring now to FIG. 5, the mask assembly 28 includes a nozzle 76 and an elbow 78. The nozzle 76 receives the hose 26 at one end and has a notch 80 (not shown) which is inserted into one end of the elbow 78. The opposite end of the elbow 78 is inserted into one of the mask cylinders 80, which generally house the filters common to such dust masks.

2. Operation of the Preferred Embodiment

To assemble the present invention, place a quantity of water 38, approximately one-fourth to one-third of the chamber volume, into the water chamber 12. Thread the cap 14 onto the wall lip 40 of the water chamber 12. Place the air inlet tube 20 into the air inlet aperture 16, positioning the lower portion of the air outlet tube 20 so as to rest below the water level. Thread the air outlet assembly 24 into the air outlet aperture 18. A user will pull downward on the slidable jacket 62 to retract the internal ball-bearings 60 and allow the nipple 68 of the industrial plug 52 to slide into the cavity 58. Once the industrial plug 52 is positioned within the cavity 58, the slidable jacket 62 is released, returning the ball-bearings 60 to a protracted position and forcibly securing the industrial plug 52.

A user will position the dust mask 30 so as to surround the mouth and chin, making sure to create a tight seal around the perimeter of the dust mask 30. The user will then breathe normally.

As the user inhales, air is pulled in through the air inlet tube 20 and into the water 38 contained within the water chamber 12. Any dust or air particulates are trapped within the water 38, and clean air is pulled out of the water 38 and into the air outlet assembly 24, travels through the hose 26 and enters the dust mask 30 through the mask coupling assembly 28, which will be further inhaled into the user's lungs. As the user inhales each time, the water 38 will bubble as it filters the contaminates from the outside air. As the user exhales, the air escapes through the cylinder 82 to the outside.

During use, if the water 38 becomes saturated with contaminants, the user may pull downward on the slidable jacket 62 to release the industrial plug 52, detach the current water chamber 12 and reattach a fresh water chamber 12' (not shown in figures) for continued operation. To reattach a fresh water chamber 12', the user will simply pull downward on the slidable jacket 62, slide the industrial plug 52 into the cavity 58, and release the slidable jacket 62 so as to secure the industrial plug 52.

After use, the water chamber 12 or chambers 12' may be emptied and cleaned for later use.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. An air filtration system comprising:

a water chamber having a threadable lip;

a threadable cat coupled to said water chamber, wherein said threadable cap forms an air inlet aperture and an air outlet aperture, wherein said cap comprises a pair of apertures formed in a planar cap top, said pair of apertures including an air inlet aperture and an air outlet aperture, said air inlet aperture receiving and housing a linearly elongated air outlet tube, said air outlet aperture receiving and housing an air outlet assembly;

an air inlet tube extending from outside said cap, into and through said can and into said water chamber at a position below water level;

a flexible hose coupled to and depending from said air outlet assembly;

a mask coupling assembly coupled to and depending from said hose;

an air mask coupled to and depending from said mask coupling assembly; and an air outlet assemble coupled to and depending from said air outlet opening, wherein said air outlet assembly comprises:

an industrial coupler, said industrial coupler includes a cavity at an upper end and a plurality of ball bearings;

an industrial plug, said industrial plug includes a plug nipple and an opposable threaded top portion, said plug nipple removably insertable into said cavity of said industrial coupler;

a female coupler, said female coupler includes a female opening for receiving said threaded top portion, said female coupler further including a tongue for insertion into a hose.

2. The air filtration system of claim 1, said industrial coupler further includes a slidably jacket with gripping tines, said slidable jacket for releasing or securing said plurality of ball bearings about said plug nipple when inserted into said industrial coupler.

3. The air filtration system of claim 1, wherein environmental air is inhaled through said air inlet tube, said environmental air being filtered by a quantity of water housed within said water chamber and filtered air is inhaled through said air outlet assembly and delivered to a user via said flexible hose.

4. The air filtration system of claim 1, wherein said water chamber comprises:

a planar base;

a curvilinear chamber wall, said base perpendicularly engaged with said chamber wall, said base and said chamber wall forming an internal chamber cavity for receiving a quantity of water.

5. The air filtration system of claim 4, wherein said chamber wall comprises a curvilinear wall lip with external threads bounding an external circumference of said wall lip.

6. The air filtration system of claim 1, wherein said cap comprises a curvilinear cap wall perpendicularly engaged with a planar cap top, said cap wall comprising internal threads bounding an internal circumference of said cap wall, said internal threads for threadably coupling said cap to said water chamber.

7. The air infiltration system of claim 1, wherein said cap comprises a pair of apertures formed in a planar cap top, said pair of apertures including an air inlet aperture and an air outlet aperture, said air inlet aperture receiving and housing a linearly elongated air outlet tube, said air outlet aperture receiving and housing an air outlet assembly.

8. The air infiltration system of claim 1, wherein said cap comprises a pair apertures formed in a planar cap top, said pair of apertures including an air inlet aperture and an air outlet aperture, said air inlet aperture receiving and housing a linearly elongated air outlet tube, said air outlet aperture receiving and housing an air outlet assembly.

9. An air filtration system comprising:

a water chamber having a threadable lip;

a threadable can coupled to said water chamber, wherein said threadable cap forms an air inlet aperture and an air outlet aperture;

an air inlet tube extending from outside said cap, into and through said cap and into said water chamber at a position below water level;

an air outlet assembly coupled to and depending from said air outlet opening;

wherein said air outlet assembly comprises:

an industrial coupler, said industrial coupler includes a cavity at an upper end and a plurality of ball bearings; an industrial plug, said industrial plug includes a plug nipple and an opposable threaded top portion, said plug nipple removably insertable into said cavity of said industrial coupler; a female coupler, said female coupler includes a female opening for receiving said threaded top portion, said female coupler further including a tongue for insertion into a hose;

a flexible hose coupled to and depending from said air outlet assembly;

a mask coupling assembly coupled to and depending from said hose;

an air mask coupled to and depending from said mask coupling assembly; and a second water chamber interchangeable with said water chamber after saturation of water contained therein.

10. The air filtration system of claim 9, wherein said water chamber comprises:

a planar base;

a curvilinear chamber wall, said base perpendicularly engaged with said chamber wall, said base and said chamber wall forming an internal chamber cavity for receiving a quantity of water.

11. The air filtration system of claim 10, wherein said chamber wall comprises a curvilinear wall lip with external threads bounding an external circumference of said wall lip.

12. The air filtration system of claim 9, wherein said cap comprises a curvilinear cap wall perpendicularly engaged with a planar cap top, said cap wall comprising internal threads bounding an internal circumference of said cap wall, said internal threads for threadably coupling said cap to said water chamber.

13. The air filtration system of claim 9, wherein said industrial coupler further includes a slidably jacket with gripping tines, said slidable jacket for releasing or securing said plurality of ball bearings about said plug nipple when inserted into said industrial coupler.

14. The air filtration system of claim 9, wherein environmental air is inhaled through said air inlet tube, said environmental air being filtered by a quantity of water housed within said water chamber and filtered air is inhaled through said air outlet assembly and delivered to user via said flexible hose.

* * * * *